(12) United States Patent
Guzman et al.

(10) Patent No.: US 8,864,399 B2
(45) Date of Patent: Oct. 21, 2014

(54) ANTISEPTIC APPLICATOR ASSEMBLY (75) Inventors: Manuel Guzman, El Paso, TX (US);
James P. McDonald, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 1089 days.

(21) Appl. No.: 12/827,631

(22) Filed: Jun. 30, 2010

(65) Prior Publication Data
US 2012/0003029 A1 Jan. 5, 2012

(51) Int. Cl.
*B43K 5/14* (2006.01)
*A61M 35/00* (2006.01)

(52) U.S. Cl.
CPC .................................. *A61M 35/003* (2013.01)
USPC ........... 401/135; 401/134; 401/132; 401/205; 604/3

(58) Field of Classification Search
CPC .................... A61M 35/006; A45D 2200/1018; A45D 2200/1009
USPC ................. 401/132–135, 205; 604/3
See application file for complete search history.

(56) References Cited

U.S. PATENT DOCUMENTS

| | | |
|---|---|---|
| 2,253,287 A | 8/1941 | Davis et al. |
| 2,361,413 A | 10/1944 | Font |
| 3,355,240 A | 11/1967 | Schwartzman |
| 3,466,131 A | 9/1969 | Arcudi |
| 3,531,300 A | 9/1970 | Greenberg et al. |
| 3,598,517 A | 8/1971 | Beecher |
| 3,619,126 A | 11/1971 | Carvallo |
| 3,725,003 A | 4/1973 | Moore at al. |
| 3,754,368 A | 8/1973 | Moore et al. |
| 3,757,782 A | 9/1973 | Aiken |
| 3,768,916 A | 10/1973 | Avery |
| 3,774,609 A | 11/1973 | Schwartzman |
| 3,986,832 A | 10/1976 | Smorenburg |
| 3,998,559 A | 12/1976 | Hoyt |
| 4,088,444 A | 5/1978 | Byrne |
| 4,183,684 A | 1/1980 | Avery, Jr. |
| 4,475,835 A | 10/1984 | Verboom et al. |
| 4,784,506 A | 11/1988 | Koreska et al. |
| 4,832,965 A | 5/1989 | Helin |
| 4,878,775 A | 11/1989 | Norbury et al. |
| 4,899,739 A | 2/1990 | Konishi |
| 4,956,962 A | 9/1990 | Williams |
| 4,963,045 A | 10/1990 | Willcox |

(Continued)

OTHER PUBLICATIONS

European Search Report dated Dec. 16, 2013.

*Primary Examiner* — David Walczak
*Assistant Examiner* — Bradley Oliver
(74) *Attorney, Agent, or Firm* — Arent Fox LLP (57) ABSTRACT

An applicator assembly includes a body defining a pocket, a closed ampoule received in the pocket, an integrated protective device attached to the body and enclosing the pocket, a lever projecting from the body, at least one tappet that bears against an external surface of the pocket and fractures the ampoule when the lever is pivoted, and an application member secured to the body, wherein an interior of the pocket is placed in fluid communication with the application member by way of through-holes provided in the integrated protective device. A method for manufacturing the applicator assembly includes rotating the protective device from an open position into a closed position to enclose the ampoule in the pocket before the application member is attached to the body so that the fluid to be dispensed will flow through the protective device and contact the application member when the ampoule is fractured.

17 Claims, 4 Drawing Sheets

(56) References Cited

U.S. PATENT DOCUMENTS

| | | | |
|---|---|---|---|
| 4,981,678 A | 1/1991 | Tomlinson | |
| 4,989,733 A | 2/1991 | Patry | |
| 5,025,123 A | 6/1991 | Pfaffmann et al. | |
| 5,103,836 A | 4/1992 | Goldstein et al. | |
| 5,117,613 A | 6/1992 | Pfaffmann | |
| 5,147,337 A | 9/1992 | Plone | |
| 5,205,110 A | 4/1993 | Buchko | |
| 5,288,159 A | 2/1994 | Wirt | |
| 5,308,180 A | 5/1994 | Pournoor et al. | |
| 5,435,660 A | 7/1995 | Wirt | |
| 5,445,462 A | 8/1995 | Johnson et al. | |
| 5,538,353 A | 7/1996 | DeHavilland | |
| 5,658,084 A | 8/1997 | Wirt | |
| D386,849 S | 11/1997 | Dehavilland | |
| 5,682,729 A | 11/1997 | Buchko | |
| 5,690,958 A | 11/1997 | McGrath | |
| 5,752,363 A | 5/1998 | Edwards et al. | |
| 5,772,346 A | 6/1998 | Edwards | |
| 5,775,826 A | 7/1998 | Miller | |
| D396,911 S | 8/1998 | Dehavilland | |
| 5,791,801 A | 8/1998 | Miller | |
| 5,927,884 A | 7/1999 | Kao | |
| 6,371,675 B1 | 4/2002 | Hoang et al. | |
| 6,916,133 B2 | 7/2005 | Hoang et al. | |
| 7,524,125 B2 * | 4/2009 | Lambert | 401/205 |
| 2006/0039742 A1 * | 2/2006 | Cable et al. | 401/134 |
| 2006/0072962 A1 * | 4/2006 | Cybulski et al. | 401/205 |

* cited by examiner

ANTISEPTIC APPLICATOR ASSEMBLY

BACKGROUND

1. Field

The present disclosure relates to an antiseptic applicator assembly, method of manufacture thereof and method of use thereof, and more particularly, to an antiseptic applicator assembly including a body having an integral protective device, a closed, liquid-filled ampoule received in the body, and an applicator member secured to the body so that liquid flows through the protective device and the applicator member when the ampoule is fractured.

2. Description of Related Art

Antiseptic applicator assemblies for the preparation of a patient prior to surgery, for example, are known and common in the prior art. Conventional applicators rely on various means of actuation to release a self-contained reservoir of antimicrobial solution for sterilization of the patient's skin. For example, a number of applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,538,353 5,658,084; 5,690,958, 5,772,346; 5,791,801; 5,927,884; 6,371,675; and 6,916,133.

The conventional applicators have been developed to include shaped walls having inward projections that engage the periphery of the ampoule to maintain the ampoule within the cavity and to prevent untoward movement of shards of glass through an applicator member when fracturing of the ampoule is effected. Further, applicators have been developed with shaped walls presenting a region to be grasped and squeezed by the user which provide a fulcruming effect so that the user squeezes the shaped wall at a location that is not directly in contact with the ampoule. In other words, the ampoule is fractured at a location that is spaced from the portion of the wall that is squeezed by the user, protecting the user from shards of the ampoule projecting through the wall. However, the possibility still exists that a user will oversqueeze the shaped wall, causing extreme fracturing of the frangible ampoule, and resulting in shards or pieces of glass, for example, penetrating through the applicator member. Although such liquid applicators represent an improvement over earlier conventional devices, there is a need to provide a liquid applicator that reduces or preferably eliminates the risk of the user being injured by shards of glass or glass particles penetrating the applicator member.

SUMMARY

In accordance with aspects of the present invention, an applicator assembly includes a body defining a pocket, a closed ampoule received in the pocket, an integrated protective device attached to the body and enclosing the pocket, a lever projecting from the body, at least one tappet that bears against an external surface of the pocket and fractures the ampoule when the lever is pivoted, and an application member secured to the body, wherein an interior of the pocket is placed in fluid communication with the application member by way of through-holes provided in the integrated protective device.

In accordance with another aspect of the present invention, the applicator assembly may include a securing mechanism for securing the protective device to the body in a closed position.

In accordance with an aspect of the present invention, a method for manufacturing the applicator assembly includes rotating the protective device from an open position into a closed position to enclose the ampoule in the pocket before the application member is attached to the body so that the fluid to be dispensed will flow through the protective device and contact the application member when the ampoule is fractured.

In accordance with yet another aspect of the present invention, a method for manufacturing an applicator assembly may include using a molding apparatus to form a body defining a pocket, releasing the body from the molding apparatus, placing a frangible ampoule into the pocket, folding a protective device laterally across the open side of the pocket, securing the protective device into a closed position, and securing the application member to the body to cover at least a portion of the protective device.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Various aspects of an antiseptic applicator assembly may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator assembly in addition to the orientation depicted in the drawings. By way of example, if an antiseptic applicator assembly in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator assembly may be illustrated with reference to one or more exemplary embodiments. As used herein, the term "exemplary" means "serving as an example, instance, or illustration," and should not necessarily be construed as preferred or advantageous over other embodiments of an antiseptic applicator assembly disclosed herein.

Figure 1:
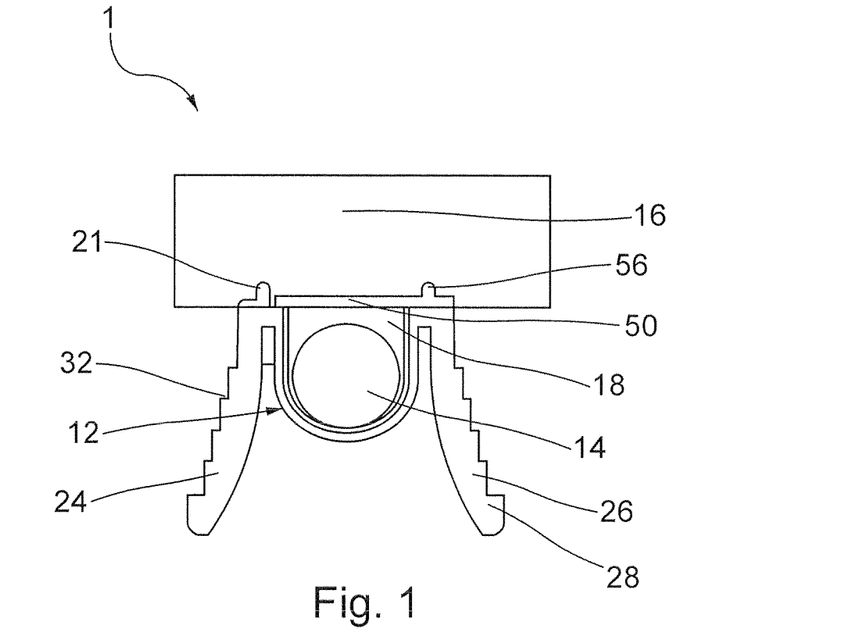
FIG. 1 is a front plan view of an antiseptic applicator, in accordance with certain aspects of the present invention.
Figure 2:
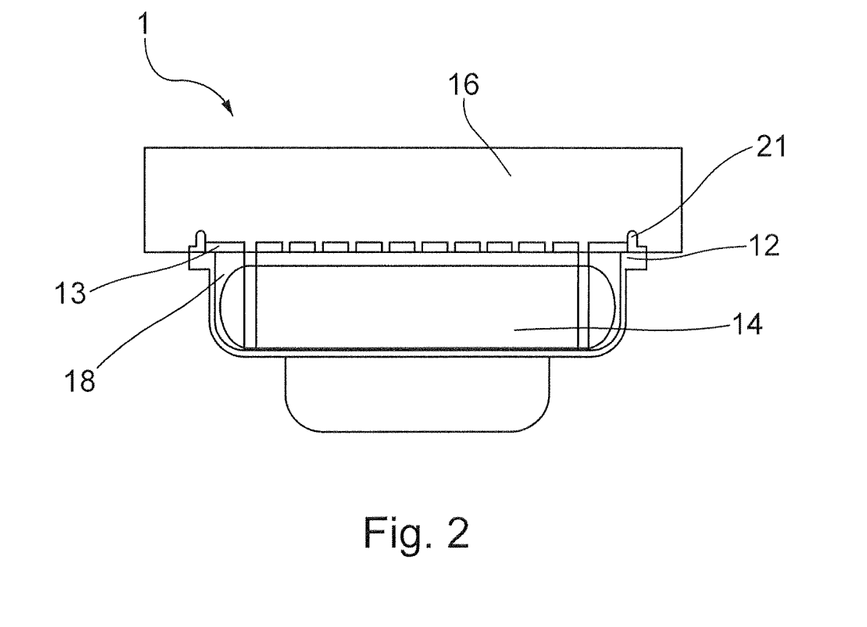
FIG. 2 is a side plan view of an antiseptic applicator, in accordance with certain aspects of the present invention.

FIGS. 1 and 2 illustrate an antiseptic applicator assembly 1 in accordance with aspects of the present invention. The applicator assembly is illustrated as broadly including a body 12 having an integral protective device 50, a closed, liquid-filled ampoule 14 received in the body 12, and an applicator member 16 secured to the body 12 so that liquid flows through the protective device 50 and the application member 16 when the ampoule 14 is fractured.

The application member 16 may be formed from a porous material, such as a sponge, for example, or any suitable material that allows the controlled application of the contained solution from the ampoule 14 to a surface external to the applicator assembly 1. The material chosen may be porous with a particular soak rate, for example, or may be provided with structural features, including slits or apertures, to direct and control the flow rate of the solution through the application member 16.

The ampoule 14 may be filled with various liquids such as antiseptics or medicaments, chemical compositions, cleansing agents, cosmetics, or the like, and preferably an antimicrobial liquid or gel composition, such as a chlorhexadine gluconate solution, for antiseptic application to a patient prior to surgery. The ampoule 14 is designed to withstand various heat and chemical sterilization techniques, which may be performed sequentially with a solution filling process, in accordance with techniques that are well known in the art. Although the ampoule 14 is illustrated as an elongated cylinder, it will be appreciated that the principles of the present invention may also be applied to spherical or elongated polygonal ampoules. Preferably, the ampoule 14 is formed of glass, although other fracturable materials are within the scope of the present invention. The wall of the glass ampoule 14 is of a thickness sufficient to contain the desired liquid during transport and storage, yet allow the ampoule to be fractured upon the application of sufficient localized pressure.

Figure 3:
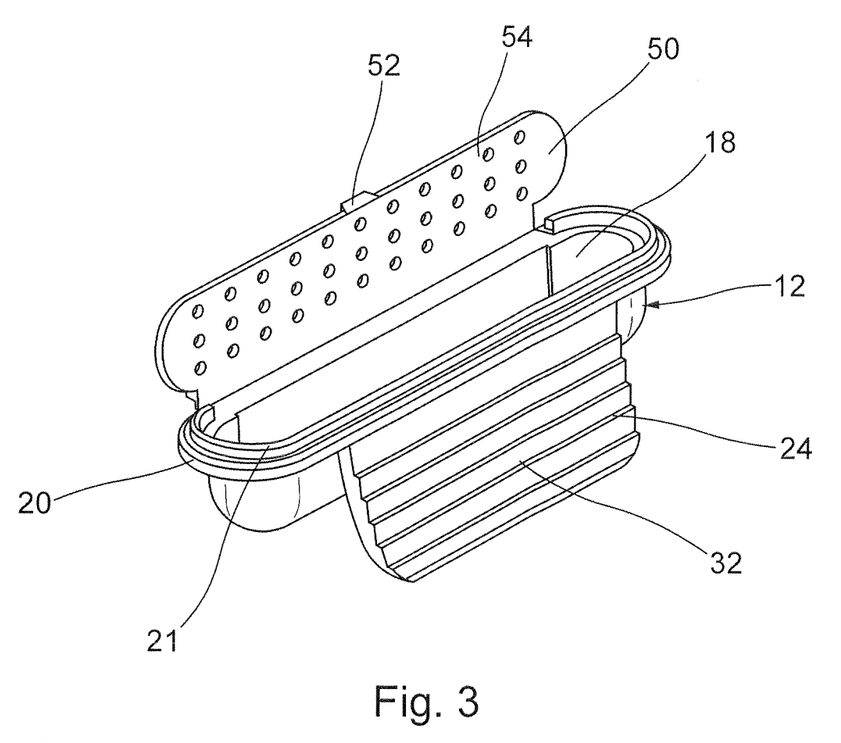
FIG. 3 is a perspective view of an exemplary antiseptic applicator, in accordance with certain aspects of the present invention.
Figure 4:
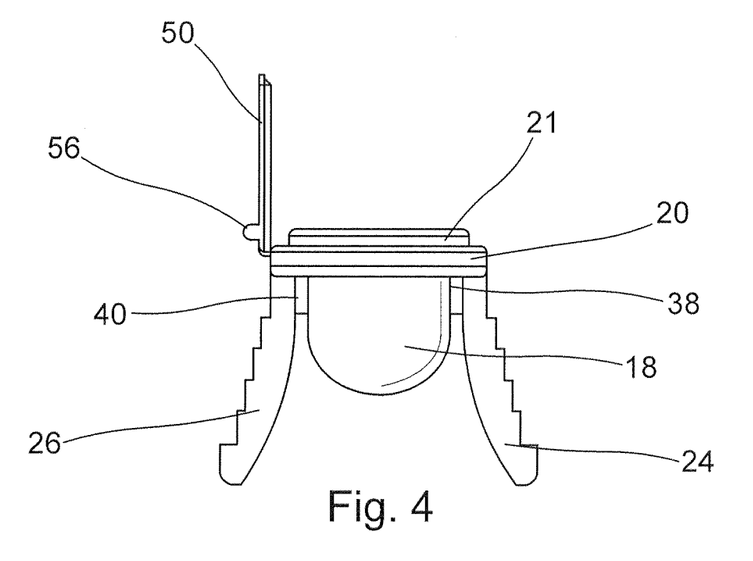
FIG. 4 is a rear view of an antiseptic applicator, in accordance with certain aspects of the present invention.

As shown in FIGS. 3 and 4, the body 12, which is preferably formed of a plastic material such as high density polyethylene or any suitable material exhibiting similar flexibility and integrity, includes an open-sided pocket 18 within which the ampoule may be received and may include a flange 20 protruding from the pocket 18 along the open side thereof. The pocket 18 has a shape generally conforming to the shape of the ampoule, as shown in FIGS. 1 and 2. Accordingly, the pocket 18 may be elongated and include a pair of laterally spaced side walls that are connected together by a U-shaped top wall. The pocket 18 defines a longitudinal axis that is generally collinear with the central longitudinal axis of the ampoule and an axial plane which includes the pocket axis and is generally parallel to the flange 20. A mounting ridge 21 may be provided to extend away from the body along a portion of a lower surface of the flange 20 surrounding the pocket 18. The mounting ridge 21, if present, may provide a surface for affixing the application member to the body 12.

As shown in FIG. 1, the body 12 also includes a pair of elongated gripping members 24, 26 projecting from the body 12 and having a wing-like configuration. The members 24, 26 may run longitudinally along a length of the pocket and are each spaced from the pocket 18 on opposite sides thereof. Along the upper free edge of each of the members 24, 26, optional ribs 28 may be provided, which extend laterally outward to facilitate handling of the applicator. Further, each of the members 24, 26 may be provided with a relatively large, textured outer surface to prevent slippage from the user's hand during application, which may take the form of a series of steps 32. As shown in FIG. 4, the flange 20 may support the gripping members 24, 26 for pivoting movement relative to the pocket 18. Accordingly, the gripping members 24, 26 define levers that may be grasped by the user and pivoted toward one another against the pocket, and this pivoting movement is accommodated by the flexibility of the material forming the body.

Figure 5:
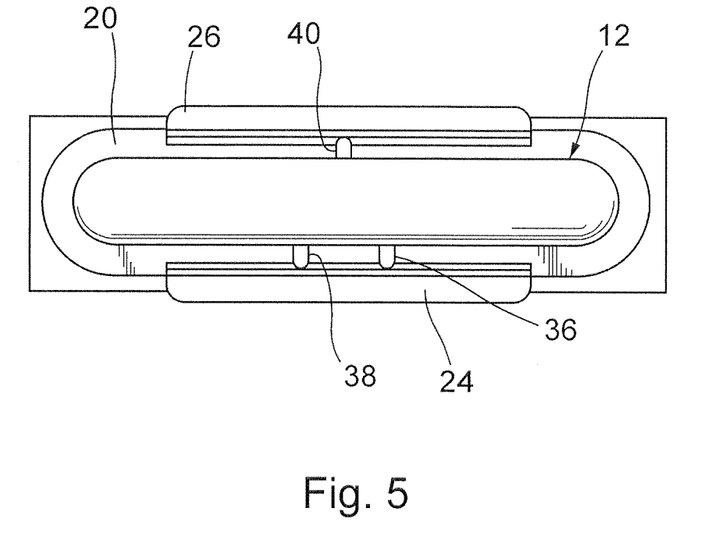
FIG. 5 is a top view of an antiseptic applicator, in accordance with certain aspects of the present invention.

As shown in FIG. 5, the body 12 also includes structure for fracturing the ampoule. Preferably, the structure includes breaking tappets 36, 38 and optionally a retaining tappet 40, interposed between the gripping members 24, 26 and the pocket 18. The breaking tappets 36, 38 interconnect the gripping member 24 and the pocket. The tappets 36, 38, 40 are arranged so that when the gripping members 24, 26 are pivoted toward one another by the user, the tappets 36, 38, 40 deform the pocket inwardly at positions immediately adjacent the tappets to exert inward forces against the ampoule. Preferably, the textured outer surfaces of the gripping members 24, 26 present a gripping area which is significantly larger than the area of the tappets which deform the pocket 18 inwardly, thereby localizing the forces effected by squeezing the members 24, 26, and enhancing fracturing of the ampoule.

More particularly, the configuration of the tappets causes the portion of the pocket extending from the axial plane to the flange to move inwardly at the tappets. The inwardly moving pocket engages the outermost point of the ampoule to exert localized fracturing forces against the ampoule that are generally vertically aligned with its central axis. The fracturing forces applied by the breaking tappets do not cause the ampoule to move toward or away from the open side of the pocket. On the other hand, the optional retaining tappet causes a portion of the pocket extending from the flange to a location between the flange and axial plane to move inwardly in the region of the retaining tappet. The inwardly moving pocket effected by the retaining tappet engages the ampoule at a point offset beneath the axial plane, thereby exerting a localized fracturing force against the ampoule which pushes the ampoule away from the open side of the pocket. Thus, the configuration of the retaining tappet maintains the ampoule within the pocket when the gripping members are pivoted toward one another to fracture the ampoule so that the ampoule does not shift prior to experiencing the localized fracturing forces being applied thereon.

As shown in FIG. 5, the optional retaining tappet may be centrally disposed along the length of the pocket. Preferably, the tappets 36, 38 are spaced axially from the retaining tappet 40 and from one another on opposite sides of the tappet 40.

The relative positioning of the tappets 36, 38, 40 concentrates the fracturing forces in a somewhat triangular pattern, enhancing the fracturing of the ampoule. However, it will be appreciated that the principles of the present invention are equally applicable to various other structure for fracturing the ampoule.

As shown in FIGS. 3 and 4, the body also includes the integrated protective device 50, which may be formed as a plate, for example, and hinged to the body 12 via the optional flange 20 along a longitudinal edge. The protective device 50 may be formed to have a shape that fully encloses the pocket 18 when the protective device 50 is folded down into a closed position (e.g., see FIG. 6). The protective device 50 may include a securing mechanism 52, such as an extended tab that snaps into a corresponding slot in the body 12 or an adhesive applied around the perimeter of the protective device 50, for example, for securing the protective device 50 in a closed position after the ampoule 14 is placed into the pocket 18. A pattern of through-holes 54 may be formed in the protective device 50 to allow passage of fluid, while preventing passage of glass shards or particles, from the internal pocket 18 to the application member. In accordance with aspects of the present invention, the through-holes 54 may be formed to be 0.05 inches in diameter, for example, and provided in an equally spaced manner over the area of the protective device 50 to permit even distribution of the fluid from the pocket 18 into the application member. In other aspects in accordance with the present invention, the protective device 50 may be provided with structural features, including slits or apertures, to direct and control the flow rate of the solution from the pocket 18 into the application member.

As shown in FIGS. 1 and 2, the pocket 18 may be formed so as to be deep enough to secure the ampoule 14 internally to the body 12 so as to avoid or minimize contact between the ampoule 14 and the protective device 50. As such, additional pressure points on the ampoule 14 from external forces applied against the protective device 50 during transportation and/or assembly, for example, may be avoided, protecting the ampoule 14 from premature fracture.

Figure 7:
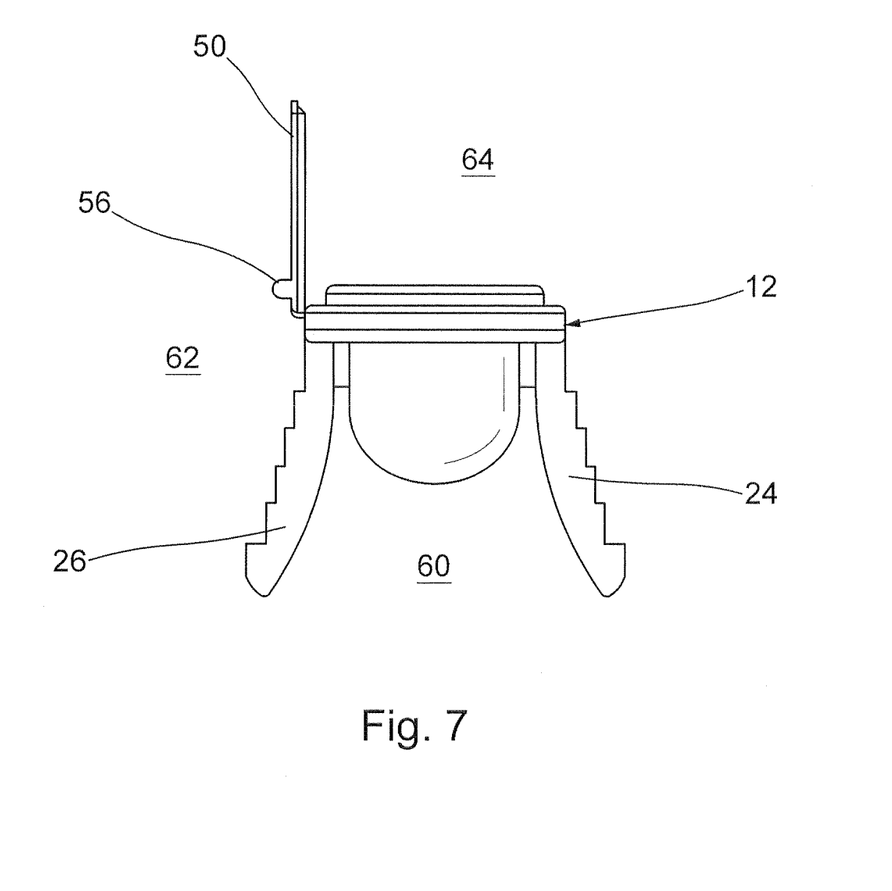
FIG. 7 is a plan view of an exemplary antiseptic applicator mold assembly, in accordance with certain aspects of the present invention.

As shown in FIG. 7, a mold may be used to form the applicator body 12 with the integrated features discussed above, in accordance with known injection molding techniques, for example. A first mold part 60, which is the stationary section, is formed to hold the body 12 by way of the pocket 18. A second mold part 62 is formed to hold an outer side of the protective device 50 and the gripping member 26. A third mold part 64 is formed to hold the inner side of the protective device 50 and the gripping member 24. Upon completion of the molding cycle, the second mold part 62 moves laterally away from the formed body 12. The third mold part 64 moves vertically away from the applicator assembly to first disengage from the internal pocket 18. Then the third mold part 64 moves laterally away from the formed body 12. The formed applicator body 12 may then be easily removed from the molding apparatus with the assistance of optional ejector pins, for example, and transferred as appropriate, either manually or automatically, for final assembly of the applicator assembly.

Figure 6:
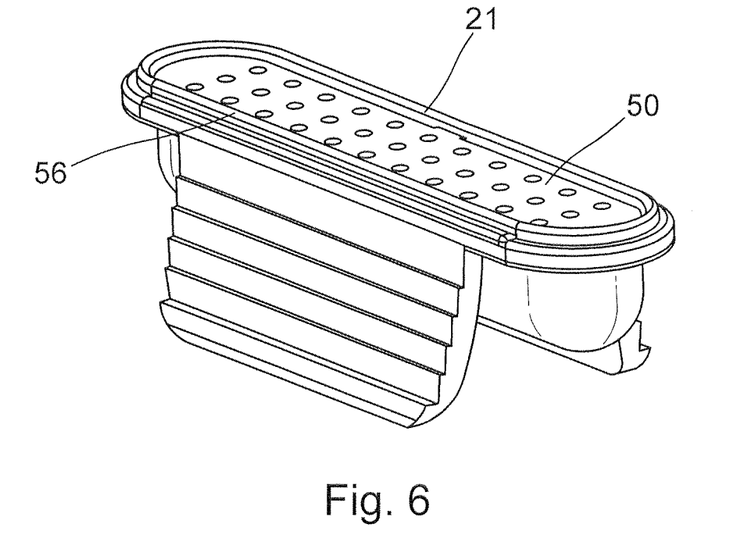
FIG. 6 is a perspective view of an exemplary antiseptic applicator, in accordance with certain aspects of the present invention.

By integrating the protective device with the body, the efficiency and cost-effectiveness of the manufacture and assembly of the applicator assembly may be enhanced. For example, by forming the integrated, hinged protective device in a 90° perpendicular plane with respect to the body and/or optional flange, an enhanced protective barrier may be provided without an increase in the number of associate parts required during the assembly process of the applicator assembly. Accordingly, the applicator assembly may be assembled by placing the body into an equipment fixture, for example, which may be a conveyor assembly. The ampoule is then placed into the pocket, either manually or automatically, and the protective device is folded laterally across the pocket so that the locking mechanism secures the protective device in a closed position while enclosing the ampoule. As shown in FIGS. 6 and 7, a welding beam 56 may be provided on the exterior surface of the protective device 50 so that when the protective device 50 is in the closed position, the welding beam 56 and the mounting ridge 21 form a continuous mounting surface along the lower surface of the body 12.

The application member may be secured to the body over the open side of the protective device so the liquid flows from the pocket, through the protective device, and through the application member when the ampoule is fractured. A laminate material, such as a polyester fabric that is resistant to stretching in one direction, referred to as the machine direction of the fabric, may be provided on the mounting side of the application member. By orienting the fabric on the application machine with the machine direction of the fabric extending in a direction perpendicular to the longitudinal axis of the pocket, the fabric resists stretching in the direction transverse to the axis of the pocket, preventing the side walls of the body from pulling apart under the squeezing force exerted on the gripping members.

The application member may be secured to the body of the applicator by welding the fabric laminate material to the body, optionally via the flange and/or the mounting ridge, if present, and the welding beam 56, using an ultrasonic welding operation, for example. The polyester material of the laminate provides suitable welding material that melts together with the material of the body to secure the application member in place over the protective device enclosing the pocket containing the ampoule. Other suitable securing expedients could be employed in place of the ultrasonic welding operation. For example, the application member could be secured in place by an adhesive, or by stitching the element in place.

In use, the applicator is designed to be grasped by the user so that the gripping members are held between the thumb or palm and fingers of one hand of the user. The members preferably include ribs and textured regions to facilitate handling of the applicator and to inhibit slippage from the user's hand. The ampoule is fractured by the user squeezing or pivoting the gripping members toward one another. The pivoting movement of the members is transferred by the tappets to the pocket to deform the pocket inwardly and exert discrete localized fracturing forces against the ampoule.

The gripping members provide a lever action that gains mechanical advantage as the members are pivoted towards one another about the flange. Accordingly, if the user has limited gripping strength, or if the wall of the ampoule is exceptionally thick, the members ensure fracturing of the ampoule.

Once the members have been sufficiently pivoted, the resulting forces fracture the ampoule releasing the liquid contained therein. At the same time, the optional retaining tappet forces the ampoule away from the open side of the pocket during fracturing which generally directs shards of glass away from the application member. Once the ampoule is fractured, liquid flows from the ampoule to the pocket, where the liquid passes through the through-holes of the protective device and ultimately into the application member. The protective device serves to further protect the application member from shards of glass carried by the liquid flowing toward the application member. The application member is then brought into contact with a surface to apply the liquid thereto.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
   a body defining a pocket;
   a closed ampoule received in the pocket, the ampoule being formed of a frangible material and containing a fluid to be dispensed;
   an integrated protective device hinged to the body and enclosing the pocket;
   a lever projecting from the body;
   at least one tappet that bears against an external surface of the pocket and fractures the ampoule when the lever is pivoted; and
   an application member secured to the body;
   wherein an interior of the pocket is placed in fluid communication with the application member by way of through-holes provided in the integrated protective device.

2. The applicator assembly of claim 1, wherein the ampoule is secured within the pocket to minimize contact with the protective device.

3. The applicator assembly of claim 1, further comprising a securing mechanism for securing the protective device to the body.

4. The applicator assembly of claim 3, wherein the securing mechanism is a tab that extends from a peripheral surface of the protective device for mating with a corresponding slot provided in the body.

5. The applicator assembly of claim 1, wherein the lever comprises two gripping members that pivot toward one another to deform the pocket inwardly to fracture the ampoule.

6. The applicator assembly of claim 1, wherein the body further comprises a mounting ridge extending from a lower surface of the body.

7. The applicator assembly of claim 6, wherein the protective device comprises a welding beam that, along with the mounting ridge, forms a continuous mounting surface extending from the lower surface of the body.

8. A method of manufacturing an applicator assembly comprising providing:
   a body defining a pocket;
   a closed ampoule received in the pocket, the ampoule being formed of a frangible material and containing a fluid to be dispensed;
   an integrated protective device hinged to the body;
   a lever projecting from the body;
   at least one tappet that bears against an external surface of the pocket and fractures the ampoule when the lever is pivoted; and
   an application member;
   wherein the integrated protective device is rotated from an open position into a closed position to enclose the ampoule in the pocket before the application member is attached to the body so that the fluid to be dispensed flows through the protective device and contacts the application member when the ampoule is fractured, and
   wherein the rotation from the open position into the closed position comprises pivoting the protective device about the hinge.

9. The method of manufacturing an applicator assembly of claim 8, wherein through-holes are provided in the protective device to permit the flow of fluid through the protective device.

10. The method of manufacturing an applicator assembly of claim 8, wherein the ampoule is secured within the pocket to minimize contact with the protective device when the protective device is placed in the closed position.

11. The method of manufacturing an applicator assembly of claim 8, further comprising a securing mechanism for securing the protective device to the body when the protective device is placed in the closed position.

12. The method of manufacturing an applicator assembly of claim 11, wherein the securing mechanism is a tab that extends from a peripheral surface of the protective device for mating with a corresponding slot provided in the body.

13. A method of manufacturing an applicator assembly comprising providing:
   a body defining a pocket;
   a closed ampoule received in the pocket, the ampoule being formed of a frangible material and containing a fluid to be dispensed;
   an integrated protective device attached to the body;
   a lever projecting from the body;
   at least one tappet that bears against an external surface of the pocket and fractures the ampoule when the lever is pivoted; and
   an application member;
   wherein the integrated protective device is rotated from an open position into a closed position to enclose the ampoule in the pocket before the application member is attached to the body so that the fluid to be dispensed flows through the protective device and contacts the application member when the ampoule is fractured,
   wherein the protective device is formed to extend at a 90° angle from the body prior to being placed in the closed position.

14. The method of manufacturing an applicator assembly of claim 8, wherein the lever comprises two gripping members that pivot toward one another to deform the pocket inwardly to fracture the ampoule.

15. The method of manufacturing an applicator assembly of claim 8, wherein the body further comprises a mounting ridge extending from a lower surface of the body.

16. The method of manufacturing an applicator assembly of claim 15, wherein the protective device comprises a welding beam that, along with the mounting ridge, forms a continuous mounting surface extending from the lower surface of the body when the protective device is placed in the closed position.

17. The applicator assembly of claim 1, wherein the through-holes are equally distributed along a length and width of the integrated protective device.

\* \* \* \* \*